United States Patent
Arranz (10) Patent No.: US 7,884,070 B2
(45) Date of Patent: Feb. 8, 2011

(54) LINEAR CATIONIC PEPTIDES HAVING ANTIBACTERIAL AND/OR ANTIFUNGAL PROPERTIES

(75) Inventor: Valérie Arranz, Monthyon (FR)

(73) Assignee: Diatos S.A., Paris (FR)

( * ) Notice: Subject to any disclaimer, the term of this patent is extended or adjusted under 35 U.S.C. 154(b) by 0 days.

(21) Appl. No.: 11/031,705

(22) Filed: Jan. 7, 2005

(65) Prior Publication Data

US 2005/0277589 A1    Dec. 15, 2005

Related U.S. Application Data

(63) Continuation of application No. PCT/FR03/002123, filed on Jul. 8, 2003.

(30) Foreign Application Priority Data

Jul. 8, 2002 (FR) ................... 02 08565

(51) Int. Cl.
- *A01N 1/00* (2006.01)
- *A01N 1/02* (2006.01)
- *A61K 38/15* (2006.01)

(52) U.S. Cl. .................. 514/2.3; 530/324; 424/404

(58) Field of Classification Search ............... 514/3, 514/13; 530/387.1
See application file for complete search history.

(56) References Cited

U.S. PATENT DOCUMENTS

| | | | |
|---|---|---|---|
| 2003/0153490 A1* | 8/2003 | Tchelingerian | 514/3 |
| 2005/0209157 A1* | 9/2005 | Owen | 514/13 |

FOREIGN PATENT DOCUMENTS

| | | |
|---|---|---|
| WO | WO 01/15511 A2 | 3/2001 |
| WO | WO 01/64738 A2 | 9/2001 |

OTHER PUBLICATIONS

Merriam-Webster reference sheet. 1 page.*
NDI Terminology reference sheet. 1 page.*
Javadpour, M., Juban, M., Wai-Chun J., Bishop, S., Alberty, J., Cowell, S., Becker, C., McLaughlin, M., "De Novo antimicrobial Peptides with Low Mammalian Cell Toxicity," J. Med. Chem., 39:3107-3113; American Chemical Society (1996).
Database NCBI 'en ligne! "Hypothetical Protein T05H4.3," 1998 Database accession No. AAB66021 XP02231078, abrégé.
FR2003/002123, Jul. 3, 2003, PCT International Preliminary Examination Report.
A. Mor, et al., "The Vertebrate Peptide Antibiotics Dermaseptins Have Overlapping Structural Features but Target Specific microorganisms," *The Journal of Biological Chemistry*, vol. 269, No. 50, pp. 31635-31641 (1994).
A.R. Alan and E.D. Earle, "Sensitivity of Bacterial and Fungal Plan Pathogens to the Lytic Peptides, MSI-99, Magainin II, and Cecropin B," *Molecular Plant-Microbe Interactions*, vol. 15, No. 7, pp. 701-708 (2002).
S. Hara and M. Yamakawa, "Moricin, a Novel Type of Antibacterial Peptide Isolated from the Silkworm, *Bombyx mori*," *The Journal of Biological Chemistry*, vol. 270, No. 50, pp. 29923-29927 (1995).
A. Polak "Transport of the Antimycotic 5-fluorocytosine and Related Substances in Fungi," *Leading Articles*, pp. 465-468.

* cited by examiner

*Primary Examiner*—Maryam Monshipouri
*Assistant Examiner*—Marsha M Tsay
(74) *Attorney, Agent, or Firm*—Hunton & Williams LLP (57) ABSTRACT

A peptide including a first peptide sequence of formula KLAKLAK (SEQ ID NO:11)in which K is lysine, L is leucine and A is alanine, and a second peptide sequence of formula (B) in which B is a peptide of 4 to 15 amino acids positively charged at neutral pH, including at least one peptide motif of formula βxxβ (SEQ ID NO:13)in which β is a basic amino acid and X is any amino acid, and in which the first peptide sequence is repeated n times and the second peptide sequence is repeated m times, n and m being whole numbers between 1 and 5.

12 Claims, 3 Drawing Sheets

SEQUENCE LISTING

<160> NUMBER OF SEQ ID NOS: 13

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Lys Arg Gly Leu Lys Leu
 1               5

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys His Leu Lys Lys His Leu Lys Lys His Leu Lys
 1               5                  10

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic

```
                        peptide

<400> SEQUENCE: 3

Gly Lys Arg Lys Lys Lys Gly Lys Leu Gly Lys Lys Arg Asp Pro
 1               5                  10                  15

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Leu Ala Lys Leu Ala Lys Lys Leu Ala Lys Leu Ala Lys
 1               5                  10

<210> SEQ ID NO 5
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(63)
<223> OTHER INFORMATION: Sequence coding peptide 1

<400> SEQUENCE: 5 gtt aaa cgt ggt ttg aaa ttg aaa ttg gct aaa ttg gct aaa aaa ttg      48
Val Lys Arg Gly Leu Lys Leu Lys Leu Ala Lys Leu Ala Lys Lys Leu
 1               5                  10                  15 gct aaa ttg gct aaa                                                  63
Ala Lys Leu Ala Lys
            20

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Lys Arg Gly Leu Lys Leu Lys Leu Ala Lys Leu Ala Lys Lys Leu
 1               5                  10                  15

Ala Lys Leu Ala Lys
            20

<210> SEQ ID NO 7
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(78)
<223> OTHER INFORMATION: Sequence coding peptide 2

<400> SEQUENCE: 7 aaa ttg gct aaa ttg gct aaa aaa ttg gct aaa ttg gct aaa aaa cat      48
Lys Leu Ala Lys Leu Ala Lys Lys Leu Ala Lys Leu Ala Lys Lys His
 1               5                  10                  15
```

```
ttg aaa aaa cat ttg aaa aaa cat ttg aaa                         78
Leu Lys Lys His Leu Lys Lys His Leu Lys
            20                  25
```

<210> SEQ ID NO 8
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

```
Lys Leu Ala Lys Leu Ala Lys Lys Leu Ala Lys Leu Ala Lys Lys His
 1               5                  10                  15

Leu Lys Lys His Leu Lys Lys His Leu Lys
            20                  25
```

<210> SEQ ID NO 9
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(87)
<223> OTHER INFORMATION: Sequence coding peptide 3

<400> SEQUENCE: 9

```
aaa ttg gct aaa ttg gct aaa aaa ttg gct aaa ttg gct aaa ggt aaa       48
Lys Leu Ala Lys Leu Ala Lys Lys Leu Ala Lys Leu Ala Lys Gly Lys
 1               5                  10                  15 cgt aaa aaa aaa ggt aaa ttg ggt aaa aaa cgt gat cct                   87
Arg Lys Lys Lys Gly Lys Leu Gly Lys Lys Arg Asp Pro
            20                  25
```

<210> SEQ ID NO 10
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

```
Lys Leu Ala Lys Leu Ala Lys Lys Leu Ala Lys Leu Ala Lys Gly Lys
 1               5                  10                  15

Arg Lys Lys Lys Gly Lys Leu Gly Lys Lys Arg Asp Pro
            20                  25
```

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

```
Lys Leu Ala Lys Leu Ala Lys
 1               5
```

<210> SEQ ID NO 12
<211> LENGTH: 110

```
<212> TYPE: PRT
<213> ORGANISM: Artificial Sequence
<220> FEATURE:
<223> OTHER INFORMATION: Description of Artificial Sequence: Synthetic
      formula sequence
<220> FEATURE:
<221> NAME/KEY: MOD_RES
<222> LOCATION: (36)..(110)
<223> OTHER INFORMATION: Any amino acid

<400> SEQUENCE: 12

Lys Leu Ala Lys Leu Ala Lys Lys Leu Ala Lys Leu Ala Lys Lys Leu
  1               5                  10                  15

Ala Lys Leu Ala Lys Lys Leu Ala Lys Leu Ala Lys Lys Leu Ala Lys
                 20                  25                  30

Leu Ala Lys Xaa Xaa Xaa Xaa Xaa Xaa Xaa Xaa Xaa Xaa Xaa Xaa Xaa
             35                  40                  45

Xaa Xaa Xaa Xaa Xaa Xaa Xaa Xaa Xaa Xaa Xaa Xaa Xaa Xaa Xaa Xaa
         50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa
            100                 105                 110

<210> SEQ ID NO 13
<211> LENGTH: 4
<212> TYPE: PRT
<213> ORGANISM: Artificial Sequence
<220> FEATURE:
<223> OTHER INFORMATION: Peptide motif
<220> FEATURE:
<221> NAME/KEY: VARIANT
<222> LOCATION: (1)..(1)
<223> OTHER INFORMATION: Xaa can be any amino acid
<220> FEATURE:
<221> NAME/KEY: VARIANT
<222> LOCATION: (2)..(3)
<223> OTHER INFORMATION: Xaa can be any basic amino acid
<220> FEATURE:
<221> NAME/KEY: VARIANT
<222> LOCATION: (4)..(4)
<223> OTHER INFORMATION: Xaa can be any amino acid

<400> SEQUENCE: 13

Xaa Xaa Xaa Xaa
  1
```

LINEAR CATIONIC PEPTIDES HAVING ANTIBACTERIAL AND/OR ANTIFUNGAL PROPERTIES

RELATED APPLICATION

This is a continuation of International Application No. PCT/FR2003/002123, with an international filing date of Jul. 8, 2003 (WO 2004/005339, published Jan. 15, 2004), which is based on French Patent Application No. 02/08565, filed Jul. 8, 2002.

FIELD OF THE INVENTION

This invention pertains to the field of the treatment of bacterial and fungal infections in humans, animals or plants. It pertains more particularly to peptides and compositions containing them for preventing and/or treating infections by pathogenic agents such as bacteria and fungi.

BACKGROUND

Numerous pathogenic microorganisms responsible for severe infections in humans and animals are resistant to the antibiotics currently used in clinical applications. The increasing development of microbial resistance is a major public health problem. Thus, during the past several years, there has been seen the development of considerable interest in the challenge of identifying new molecules, particularly for the study of short peptides 15 to 30 amino acids possessing antibacterial and antifungal activities—and having a mode of action different from the conventionally used antibiotics. Numerous peptides derived from human, animal and plant proteins are known to possess antimicrobial properties while others are generated synthetically on the basis of physico-chemical studies.

The 14-mer linear peptide of sequence KLAKLAKKLAK-LAK (SEQ ID NO: 4) was described in the literature as a nonhemolytic peptide having antibacterial activity (Javadpour MM, Juban, MM, Lo WC et al. De novo antimicrobial peptides with low mammalian cell toxicity. J Med Chem Aug. 2, 1996; 39(16): 3107-13). The limited studies carried out on that peptide showed activity against three strains of bacteria (*E. coli*, *P. aeruginosa* and *S. aureus*) during a short incubation period of 4 hours. Results with longer incubation periods have not been reported.

SUMMARY OF THE INVENTION

This invention relates to a peptide including a first peptide sequence of formula (KLAKLAK (SEQ ID NO: 11)) in which K is lysine, L is leucine and A is alanine, and a second peptide sequence of formula (B) in which B is a peptide of 4 to 15 amino acids positively charged at neutral pH, including at least one peptide motif of formula $\beta xx\beta$ (SEQ ID NO: 13) in which $\beta$ is a basic amino acid and X is any amino acid, and in which the first peptide sequence is repeated n times and the second peptide sequence is repeated m times, n and m being whole numbers between 1 and 5.

This invention also relates to a pharmaceutical composition including a therapeutically effective amount of an active agent including at least one peptide and a carrier.

This invention further relates to a polynucleotide coding for the at least one peptide.

This invention still further relates to a nucleic acid molecule as a vector including the at least one polynucleotide.

This invention also further relates to a host including an animal or plant cell or a prokaryote and the nucleic acid molecule.

This invention yet again relates to a plant generated from the plant cell.

BRIEF DESCRIPTION OF THE DRAWINGS

Other advantages and characteristics of the invention will become apparent from the examples below presented for illustrative purposes with reference to the attached drawings in which.

DETAILED DESCRIPTION

I performed in vitro studies of the antibacterial properties of the 14-mer linear peptide under standard evaluation conditions (incubation of 18 hours) which did not reveal any biological activity at the concentrations described in the literature. In contrast, I unexpectedly discovered that KLAKLAK (SEQ ID NO: 11) is capable of conferring antibacterial and/or antifungal properties on peptides comprising this motif and a peptide sequence not having antibacterial and/or antifungal properties.

The invention thus provides a peptide, which is advantageously linear and cationic, comprising:

a first peptide sequence of formula (KLAKLAK (SEQ ID NO: 11)) in which K is the amino acid lysine, L is the amino acid leucine and A is the amino acid alanine, and a second peptide sequence of formula (B) in which B is a peptide of 4 to 15 amino acids positively charged at neutral pH, comprising at least one peptide motif of formula $\beta xx\beta$ (SEQ ID NO: 13) in which $\beta$ is a basic amino acid and X is any amino acid, and in which the first peptide sequence is repeated n times and the second peptide sequence is repeated m times, n and m being whole numbers between 1 and 5, with n preferably being a whole number between 1 and 3, and m advantageously being greater than 1; the second peptide sequences (B) are identical or different.

The peptides of the invention can thus comprise multiple second peptide sequences (B), which can be identical or different, and thus multiple peptide motifs of formula $\beta xx\beta$ (SEQ ID NO: 13), which can be identical or different, in each of the second peptide sequences (B).

The peptides of the invention are advantageously linear. They thus respond to the following general formula (I):

(KLAKLAK(SEQ ID NO: 12))n(B)m in which the first and second peptide sequences are:

alternating, or grouped at one and/or the other of the N and C terminal ends of one of the first or second peptide sequences.

In the peptides of the invention, the first peptide sequence(s) is(are) preferably grouped at one and/or the other of the N and C terminal ends of the second peptide sequence(s). The first and second peptide sequences are preferably linked together by covalent bonds, advantageously peptidic bonds.

In the peptide motif of formula βxx, β is a basic amino acid preferably selected from the group comprising arginine (R) and lysine (K) and X is preferably selected from the group comprising leucine (L), glycine (G) and histidine (H).

As specific examples of the second peptide sequence entering into the composition of the peptides according to the invention, the following sequences can be cited:

```
SEQ ID No. 1:    VKRGLKL
SEQ ID No. 2:    KHLKKHLKKHLK
SEQ ID No. 3:    GKRKKGKLGKKRDP
```

These second peptide sequences can be associated with a first peptide sequence repeated twice: KLAKLAKKLAK-LAK (SEQ ID No.4) to generate linear cationic peptides having an antibacterial and/or antifungal activity after 18 hours of incubation with the microorganisms.

The peptides of the invention can be prepared by chemical synthesis or by genetic engineering in a prokaryote cell such as a bacterium, in a eukaryote cell such as a yeast, a CHO cell, an NSO cell, in a transgenic animal, e.g., in the milk of a transgenic rabbit, goat or ewe or the like, or in a transgenic plant such as, for example, tobacco plants or the like.

The invention thus also pertains to the functional equivalents of the peptides defined above, such as peptides comprising modifications stemming from post-translational processes such as glycosylation or chemical modifications such as coupling with lipids, sugars, nucleotide sequences as long as the modifications do not modify the antibacterial and/or antifungal antibacterial activity of the peptides in conformity with the tests presented in the experimental part below. The functional equivalents also comprise peptides of which one or more amino acids are amino acids of D conformation. The invention also covers retro-peptides and retro-inverso-peptides.

The invention also uses the peptides in humans, animals or plants for preventing and/or treating a bacterial and/or fungal infection. The invention thus pertains to a pharmaceutical, cosmetic or food-processing composition comprising as active principle at least one peptide as defined above combined in the composition with one or more pharmaceutically acceptable vehicles, diluents, excipients or the like. The peptides of the invention have low toxicity and moreover are nonhemolytic.

The vehicles, diluents and excipients are selected as a function of the type of application of the composition whether it be pharmaceutical, cosmetic or agricultural.

The invention thus also uses a peptide as defined above for the preparation of a pharmaceutical, cosmetic, dermatological or food-processing composition with antibacterial and/or antifungal intent.

The peptides of the invention possess antibacterial activity against a large variety of microorganisms including activity against Gram-negative bacteria, Gram-positive bacteria, filamentous fungi and yeasts whereas the second and first sequences taken in isolation do not have activity under the selected evaluation conditions.

The compositions of the invention are useful both with preventive and curative intent.

Administration of pharmaceutical compositions according to the invention can be implemented by any of the modes of administration accepted for therapeutic agents. These methods comprise systemic, topical or central administration, e.g., via intracranial surgical pathway or intraocular administration. The subcutaneous implantation of biodegradable implants can also be cited.

Oral administration can be implemented by means of tablets, capsules, soft capsules, including delayed or prolonged release formulations, pills, powders, granulates, elixirs, tinctures, suspensions, syrups, emulsions and the like. This form of presentation is particularly suitable for passage across the intestinal barrier and is the most common form of administration of antibacterial and/or antifungal compounds.

Parenteral administration of antibacterial and/or antifungal compounds is generally implemented via intramuscular injection or via the intravenous route by perfusion. Injectable compositions can be prepared in conventional forms either in suspension or liquid solution or in solid form suitable for dissolution in a suitable liquid at time of use, including delayed and prolonged release formulations such as the incorporation of the peptides in biodegradable microparticles or nanoparticles of lipidic formulation or dextran formulation or PLGA formulation or equivalents thereof. This form of presentation is more particularly suitable for passage across the blood-brain barrier and hospital use of antibacterial and/or antifungal compounds.

One possibility for parenteral administration uses the implantation of a slow or prolonged release system which provides for the maintenance of a substantially constant dose level.

Another possibility comprises fixing by adsorption or other method the peptides of the invention on a support, such as a catheter, prosthesis or biological glue.

Suitable intranasal vehicles can be used for intranasal administration.

Other conventional topical preparations comprise creams, unguents, lotions, gels, aerosol sprays and the like. The aerosol sprays are especially suitable for the treatment of bacterial and/or fungal bronchopulmonary infections.

The use of the peptides of the invention in cosmetic compositions is useful for essentially preventive purposes consisting of incorporating the peptides in creams, nail polish, hygiene products for the genital organs, toothpastes, buccal hygiene products or of incorporating them in slow diffusion microparticles, in aqueous phase, including for example disposable diapers, cotton swabs, dressings, make-up remover pads, sanitary napkins or litter for animals.

The compounds can be in solid, semisolid or liquid form as a function of the mode of administration.

For solid compositions, such as tablets, pills, powders or granulates in the free state or incorporated in capsules, the active principle can be combined with:

diluents, e.g., lactose, dextrose, sucrose, mannitol, sorbitol, cellulose and/or glycine;

lubricants, e.g., silicon, talc, stearic acid, its magnesium or calcium salt and/or polyethyleneglycol;

binders, e.g., magnesium and aluminum silicate, starch paste, gelatin, tragacanth gum, methylcellulose, sodium carboxymethylcellulose and/or polyvinylpyrrolidone; if needed, disintegration agents, e.g., starch, agar, alginic acid or its sodium salt, or effervescent mixtures; and/or adsorbents, colorants, flavoring agents and sweeteners. The excipients can be, e.g., mannitol, lactose, starch, magnesium stearate, sodium saccharin, talc, cellulose, glucose, sucrose, magnesium carbonate and analogues of pharmaceutical quality.

For semisolid compositions, such as suppositories, the excipient can be, e.g., an emulsion or fatty suspension, or based on a polyalkylene glycol such as polypropylene glycol.

The liquid compositions, in particular for injectables or to be incorporated in a soft capsule, can be prepared, e.g., by dissolution, dispersion, etc. of the active principle in a pharmaceutically pure solvent such as, e.g., water, physiological serum, aqueous dextrose, glycerol, ethanol, an oil and similar products.

The peptides according to the invention can also be administered in the form of release systems of the liposome type, such as in the form of small unilamellar vesicles, large unilamellar vesicles and multilamellar vesicles. The phospholipids can be formed from a variety of phospholipids containing cholesterol, stearylamine or phosphatidylcholines. In one form of execution, a film of liquid components can be hydrated with an aqueous solution of the drug to form a lipidic layer encapsulating the drug.

The compositions according to the invention can be sterilized and/or contain nontoxic adjuvants and auxiliary substances such as preservatives, stabilization agents, wetting or emulsification agents, agents promoting dissolution, salts for regulating the osmotic pressure and/or buffers. The compositions can moreover also contain other substances having therapeutic value. The compositions are prepared respectively by the conventional processes of mixing, granulation or coating and they contain about 0.1 to about 75%, preferably about 1 to about 50%, of active principle.

The peptides according to the invention can also be coupled with soluble polymers such as targetable drug supports. Such polymers can comprise polyvinylpyrrolidone, pyrane copolymer, poly(hydroxypropyl)-methacrylamide-phenol, poly(hydroxyethyl)-aspanamide-phenol or poly(ethylene oxide)-polylysine substituted by palmitoyl residues, dextran. The compounds according to the invention can furthermore be coupled to a class of biodegradable polymers useful for creating a controlled release of a drug, e.g., poly (lactic acid), poly(epsilon-caprolactone), poly(hydroxybutyric acid), the polyorthoesters, the polyacetals, the polydihydropyranes, the polycyanoacrylates and the cross-linked or amphipathic sequenced hydrogel copolymers.

The dosage for the administration of the peptides according to the invention is selected as a function of numerous factors including the type, species, age, weight, sex and medical condition of the subject; the gravity of the condition to be treated; the route of administration; the state of the renal and hepatic functions of the subject and the nature of the particular compound or salt employed. A normally experienced physician or veterinarian can easily determine and prescribe the effective amount for treating, impeding or stopping the progress of the medical condition to be treated.

A composition according to the invention can contain from about 0.1 to about 99%, preferably about 1 to about 70%, of active principle.

As examples, the oral dosages of the peptides according to the invention can be between about 0.5 and about 1 mg/day via the oral route and preferably provided in the form of tablets containing about 0.5, about 1, about 2.5, about 5, about 10, about 15, about 25, about 50, about 100, about 250, about 500 and about 1000 mg of active principle. The effective plasma concentrations of peptides will be obtained starting at a dosage ranging from about 0.002 mg to about 50 mg per kg of body weight per day.

The peptides according to the invention can be administered in the form of a single daily dose or in two, three or four doses per day.

The invention envisages not only the administration of the previously described peptides, but also the use of polynucleotide sequences coding these peptides for transforming hosts, notably animal or plant cells, or prokaryotes. These sequences are used in conformity with the genetic engineering techniques described in the literature.

The invention consequently also provides a polynucleotide coding a peptide described above, a molecule of nucleic acid, DNA or RNA, as a vector comprising said polynucleotide and a host, e.g., an animal or plant cell or a prokaryote comprising the molecule of nucleic acid as well as the notably pharmaceutical compositions containing them.

The following can be cited as examples of such polynucleotides that can be used for transforming plant or animal cells or prokaryotes:

```
the sequence
5' GTT AAA CGT GGT TTG AAA TTG AAA    (SEQ ID No. 5)
TTG GCT AAA TTG GCT AAA AAA TTG
GCT AAA TTG GCT AAA 3', coding the peptide
VKRGLKLKLAKLAKKLAKLAK,                (SEQ ID No. 6)

the sequence
5' AAA TTG GCT AAA TTG GCT AAA AAA    (SEQ ID No. 7)
TTG GCT AAA TTG GCT AAA AAA CAT
TTG AAA AAA CAT TTG AAA AAA CAT
TTG AAA 3' coding the peptide
KLAKLAKKLAKLAKKHLKKHLKKHLK,           (SEQ ID No. 8)

the sequence
5' AAA TTG GCT AAA TTG GCT AAA AAA    (SEQ ID No. 9)
TTG GCT AAA TTG GCT AAA GGT AAA
CGT AAA AAA AAA GGT AAA TTG GGT
AAA AAA CGT GAT CCT 3' coding the peptide
KLAKLAKKLAKLAKGKRKKKGKLGKKRDP.        (SEQ ID No. 10)
```

The invention thus also pertains to agricultural applications of the previously described peptides for rendering plants resistant to phytopathogenic bacteria and fungi, thereby reducing the preventive or curative use of chemical pesticides which are toxic for the environment. The direct application on the plant of an effective amount of antibacterial and/or antifungal peptides or of composition containing them represents a first form of implementation of the agricultural application. A second form of implementation of this application is based on transgenic techniques comprising incorporating in a stable manner in the DNA of a plant cell a polynucleotide sequence coding for one or more of the antibacterial and/or antifungal peptides described above. The plant cells transformed in this manner make it possible to regenerate a plant thereby transmitting the character of resistance to bacterial and/or fungal infections to its descendants. As examples of plants, we can cite rice, corn, rape, beet, wheat, tobacco, tomato, potato and the like.

The amino acids are generally represented by their single letter code but they can also be represented by their three-letter code according to the nomenclature below:

| | | |
|---|---|---|
| A | Ala | Alanine |
| C | Cys | Cysteine |
| D | Asp | Aspartic acid |
| E | Glu | Glutamic acid |
| F | Phe | Phenylalanine |

-continued

| | | |
|---|---|---|
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Material

1. Linear Peptides

```
No. 1:
VKRGLKLKLAKLAKKLAKLAK          (SEQ ID No. 6)

No. 2:
KLAKLAKKLAKLAKKHLKKHLKKHLK     (SEQ ID No. 8)

No. 3:
KLAKLAKKLAKLAKGKRKKKGKLGKKRDP  (SEQ ID No. 10)
```

2. Bacteria, Filamentous Fungi and Yeasts

The strains used and referenced in the various results were obtained from the collection banks of the ATCC (American Type Culture Collection) and the Pasteur Institute.

3. Cells

Human red blood cells stemming from total blood obtained from the French Blood Agency [Etablissement Francais du Sang] (EFS) and stored at +4° C.

4. Preparation of the Peptides

The peptide syntheses were performed according to the techniques known by the expert in the field. The peptides are water soluble.

Results

I. Evaluation of the Antimicrobial Activity of the Peptides

A. Determination of the Minimal Inhibitory Concentration (MIC) and the Minimal Bactericidal Concentration (MBC) in Liquid Medium The MIC values were determined by the method of microdilution in liquid medium (NCCLS M7A5) for all of the bacterial species on 96-well polystyrene plates.

The culture medium was Mueller-Hinton broth (MHB) (pH≈7.2-7.4) with supplements according to the bacterial species studied:

MHB alone for the non-exigent species,
MHB+3% lysed horse blood for the streptococci, Listeria and Neisseria,
MHB+hemin 15 mg/l+NAD 15 mg/l+yeast extract 5 g/l for Haemophilus.

The bacterial inoculum was prepared from re-isolation performed on:

CLED agar: non-exigent strains,
blood agar+5% goat blood: streptococci, Listeria and Neisseria
chocolate agar+5% goat blood: Haemophilus, Neisseria.

The final inoculum was at ≈5·10$^5$ cfu/ml (colony forming units). 50 µl of bacterial inoculum was distributed per well containing an equal volume of the peptide solution diluted by half in the appropriate culture medium depending on the bacterial species (0.5 to 512 µg/ml). The cultures were incubated at 35° C. in ambient air for 16 to 20 hours (20 to 24 h for the streptococci).

The MIC value expressed in µg/ml was the first concentration not exhibiting bacterial growth.

Determination of the MBC values was performed after inhibition and reading of the MIC plates:

A volume of 3 µl of each concentration of antibiotic was deposited on the agar media:

MH: for the non-exigent strains,
MH+5% sheep blood: for the streptococci, Listeria, Bacillus and Neisseria,
HTM: for the Haemophilus.

The agars were incubated for 18 h at 35° C. in atmosphere:
in ambient air: for the non-exigent strains,
with 5-6% of $CO_2$: for the streptococci, Listeria, Haemophilus and Neisseria.

The MBC is the lowest concentration of antibiotic that inhibits all bacterial growth on the transplant agar (<0. 1% of survivors).

Table 1 below shows the activity of the peptides against the bacteria.

The results show clearly that peptide no. 2 is more active than peptide no. 1. Peptide no. 3 is not active.

The MBC values are very close to the MIC values: the MBC/MIC ratio is often equal to 2, rarely greater than 4 which is indicative of a bactericidal activity of peptides no. 1 and no. 2.

TABLE 1

| BACTERIA | ATCC No. | Peptide 1 | | Peptide 2 | | Peptide 3 | |
|---|---|---|---|---|---|---|---|
| | | MIC | MBC | MIC | MBC | MIC | MBC |
| Gram-negative bacteria | | | | | | | |
| Acinetobacter baumanii | 19606 | 8 | 16 | 2 | 2 | nt | nt |
| Citrobacter freundii | 8090 | 16 | 16 | 8 | 8 | nt | nt |
| Enterobacter aerogenes | 13048 | 256 | 256 | 16 | 16 | nt | nt |
| Enterobacter cloacae | 23355 | 16 | 16 | 2 | 2 | nt | nt |
| Escherichia coli | 25922 | 16 | 16 | 2 | 2 | nt | nt |
| Escherichia coli | 35218 | 8 | 8 | 2 | 2 | 64 | nt |
| Haemophilus influenzae | 49247 | 64 | 64 | 32 | 32 | nt | nt |
| Klebsiella pneumoniae | 13883 | >512 | >512 | 32 | 32 | nt | nt |
| Listeria monocytogenes | 19115 | 128 | 128 | 2 | 2 | nt | nt |
| Neisseria sica | 9913 | 4 | 128 | 0.5 | 0.5 | nt | nt |
| Proteus vulgaris | 13315 | 128 | 256 | 4 | 4 | nt | nt |

TABLE 1-continued

| BACTERIA | ATCC No. | Peptide 1 MIC | Peptide 1 MBC | Peptide 2 MIC | Peptide 2 MBC | Peptide 3 MIC | Peptide 3 MBC |
|---|---|---|---|---|---|---|---|
| *Pseudomonas aeruginosa* | 27853 | 512 | >512 | 8 | 8 | 64 | nt |
| *Salmonella typhimurium* | 14028 | 8 | 8 | 4 | 4 | nt | nt |
| *Serratia marcescens* | 8100 | >512 | >512 | >512 | >512 | nt | nt |
| *Shigella flexneri* | 112022 | 16 | 32 | 2 | 2 | nt | nt |
| *Shigella sonnei* | 25931 | 4 | 4 | 2 | 2 | nt | nt |
| Gram-positive bacteria | | | | | | | |
| *Bacillus cereus* | 11778 | 128 | 128 | 8 | 8 | nt | nt |
| *Bacillus subtilis* | 6633 | 8 | 8 | 8 | 8 | nt | nt |
| *Enterococcus faecalis* | 19433 | >512 | >512 | 64 | 128 | nt | nt |
| *Enterococcus faecalis* | 29212 | >512 | >512 | 32 | 32 | 64 | nt |
| *Enterococcus faecium* | 35667 | 128 | >512 | 16 | 32 | nt | nt |
| *Micrococcus luteus* | 9341 | 4 | 4 | 4 | 4 | nt | nt |
| *Staphylococcus aureus* | 14154 | 64 | 128 | 32 | 64 | nt | nt |
| *Staphylococcus aureus* | 25923 | 64 | 64 | 16 | 32 | 64 | nt |
| *Staphylococcus epidermidis* | 12228 | 4 | 4 | 2 | 2 | nt | nt |
| *Streptococcus agalactiae* | 13813 | 128 | 128 | 8 | 8 | nt | nt |
| *Streptococcus pneumoniae* | 6303 | 64 | 64 | 32 | 128 | >500 | nt |
| *Streptococcus pneumoniae* | 49619 | 128 | 256 | 16 | 256 | nt | nt |
| *Streptococcus pyogenes* | 19615 | 64 | 64 | 8 | 8 | nt | nt | nt: not tested

Table 2 below shows the antibacterial activity of peptides 1 and 2 determined on a collection of clinically pathogenic strains possessing in some cases known mechanisms of resistance to antibiotics.

These results confirm that peptide 2 is more active. These results furthermore clearly show that there is no crossed resistance mechanism between peptide 2 and the antibiotics currently used in clinic.

TABLE 2

| Clinical strain of bacteria | Resistance phenotype | Peptide 1 MIC | Peptide 1 MBC | Peptide 2 MIC | Peptide 2 MBC |
|---|---|---|---|---|---|
| Gram-negative bacteria | | | | | |
| *Acinetobacter baumanii* | susceptible | 8 | 8 | 2 | 2 |
| *Acinetobacter baumanii* | susceptible | 8 | 16 | 2 | 8 |
| *Acinetobacter baumanii* | susceptible | 4 | 8 | 2 | 8 |
| *Acinetobacter baumanii* | penicillinase + cephalosporinase | 8 | 8 | 4 | 4 |
| *Acinetobacter baumanii* | penicillinase + cephalosporinase | 4 | 8 | 2 | 2 |
| *Acinetobacter baumanii* | penicillinase + cephalosporinase | 8 | 8 | 2 | 2 |
| *Acinetobacter baumanii* | cephalosporinase | 4 | 4 | 2 | 2 |
| *Acinetobacter baumanii* | cephalosporinase | 8 | 8 | 2 | 2 |
| *Acinetobacter baumanii* | cephalosporinase | 4 | 4 | 2 | 2 |
| *Enterobacter cloacae* | cephalosporinase | 8 | 8 | 2 | 2 |
| *Enterobacter cloacae* | desuppressed cephalosporinase | 16 | 32 | 8 | 8 |
| *Enterobacter cloacae* | desuppressed cephalosporinase | 16 | 16 | 4 | 4 |
| *Enterobacter cloacae* | desuppressed cephalosporinase | 16 | 16 | 4 | 4 |
| *Enterobacter aerogenes* | cephalosporinase | 512 | >512 | 4 | 8 |
| *Enterobacter aerogenes* | desuppressed cephalosporinase | 512 | >512 | 8 | 8 |
| *Enterobacter aerogenes* | desuppressed cephalosporinase | >512 | 512 | 8 | 8 |

TABLE 2-continued

| Clinical strain of bacteria | Resistance phenotype | Peptide 1 MIC | Peptide 1 MBC | Peptide 2 MIC | Peptide 2 MBC |
|---|---|---|---|---|---|
| *Enterobacter aerogenes* | Enlarged spectrum beta lactamase | 128 | 512 | 4 | 8 |
| *Escherichia coli* | susceptible | 4 | 4 | 1 | 1 |
| *Escherichia coli* | susceptible | 256 | 512 | 4 | 4 |
| *Escherichia coli* | penicillinase | 8 | 16 | 2 | 2 |
| *Escherichia coli* | penicillinase | 256 | 256 | 4 | 4 |
| *Escherichia coli* | cephalosporinase | 32 | 32 | 2 | 2 |
| *Escherichia coli* | cephalosporinase | 32 | 32 | 4 | 4 |
| *Escherichia coli* | Enlarged spectrum beta lactamase | 64 | 64 | 4 | 4 |
| *Escherichia coli* | Enlarged spectrum beta lactamase | 32 | 32 | 2 | 2 |
| *Listeria monocytogenes* | — | 8 | 16 | 2 | 2 |
| *Listeria monocytogenes* | — | 8 | 16 | 2 | 4 |
| *Listeria monocytogenes* | — | 8 | 16 | 2 | 4 |
| *Listeria monocytogenes* | — | 16 | 16 | 2 | 4 |
| *Listeria monocytogenes* | — | 8 | 16 | 2 | 4 |
| *Listeria monocytogenes* | — | 16 | 16 | 4 | 16 |
| *Listeria monocytogenes* | — | 8 | 8 | 2 | 2 |
| *Listeria monocytogenes* | — | 16 | 32 | 4 | 4 |
| *Pseudomonas aeruginosa* | susceptible | 64 | >512 | 8 | 8 |
| *Pseudomonas aeruginosa* | susceptible | 32 | 64 | 2 | 4 |
| *Pseudomonas aeruginosa* | susceptible | 256 | >512 | 4 | 4 |
| *Pseudomonas aeruginosa* | susceptible | 64 | >512 | 4 | 8 |
| *Pseudomonas aeruginosa* | penicillinase | 512 | >512 | 4 | 8 |
| *Pseudomonas aeruginosa* | penicillinase | 32 | 256 | 8 | 8 |
| *Pseudomonas aeruginosa* | penicillinase | 64 | 512 | 4 | 4 |
| *Pseudomonas* | cephalosporinase | 128 | >512 | 8 | 8 |

TABLE 2-continued

| Clinical strain of bacteria | Resistance phenotype | Peptide 1 MIC | Peptide 1 MBC | Peptide 2 MIC | Peptide 2 MBC |
|---|---|---|---|---|---|
| aeruginosa Pseudomonas aeruginosa | cephalosporinase | 128 | >512 | 8 | 8 |
| Pseudomonas aeruginosa | resistance to imipenem | 32 | 32 | 4 | 4 |
| Gram-positive bacteria | | | | | |
| Staphylococcus epidermidis | susceptible to methicillin | 4 | 8 | 4 | 4 |
| Staphylococcus epidermidis | susceptible to methicillin | 4 | 8 | 2 | 2 |
| Staphylococcus epidermidis | susceptible to methicillin | 2 | 4 | 2 | 2 |
| Staphylococcus epidermidis | susceptible to methicillin | 4 | 4 | 2 | 2 |
| Staphylococcus epidermidis | resistance to methicillin | 4 | 4 | 2 | 2 |
| Staphylococcus epidermidis | resistance to methicillin | 4 | 4 | 2 | 2 |
| Staphylococcus epidermidis | resistance to methicillin | 4 | 4 | 2 | 2 |
| Staphylococcus epidermidis | resistance to methicillin | 4 | 4 | 2 | 2 |

B. Kinetic study of the Antibacterial Activity

An isolated colony of the bacterium *E. coli* ATCC 25922 or *P. aeruginosa* ATCC 27853 was suspended in 3 to 5 ml of Mueller-Hinton (MH) culture medium and incubated at 37° C. overnight under agitation. A culture in exponential phase of growth of the strain was prepared based on this overnight culture; the MH medium was seeded at 1/50$^{th}$ with the overnight culture and incubated for 2 hours at 37° C. under agitation. The bacterial concentration was adjusted to $1\text{-}2\cdot 10^6$ cfu/ml (colony forming units) in the MH medium.

$1\cdot 10^5\text{-}1\cdot 10^6$ cfu were incubated at 37° C. in the presence of or without peptides (x µg/ml) for increasing periods of time (30 minutes, 1 hour, 3 hours and 6 hours) in a final volume of 10 ml of MH. The number of cfu at these different durations of incubation was evaluated by spreading 500 µl of the bacterial suspension on a dish of MH agar which was incubated at 37° C. for 18 hours.

Figure 1:
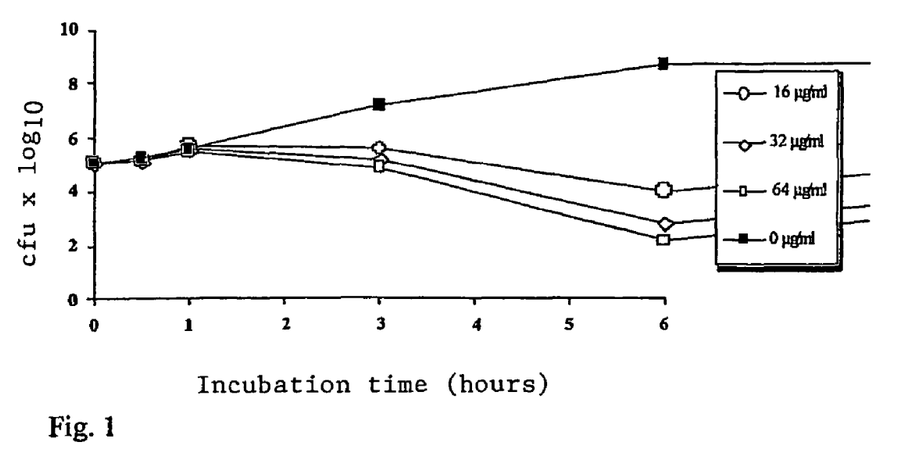
FIG. 1 is a graph showing the kinetic of bactericidal activity of peptide no. 1 of SEQ ID No. 6 on *E. coli*.
Figure 2:
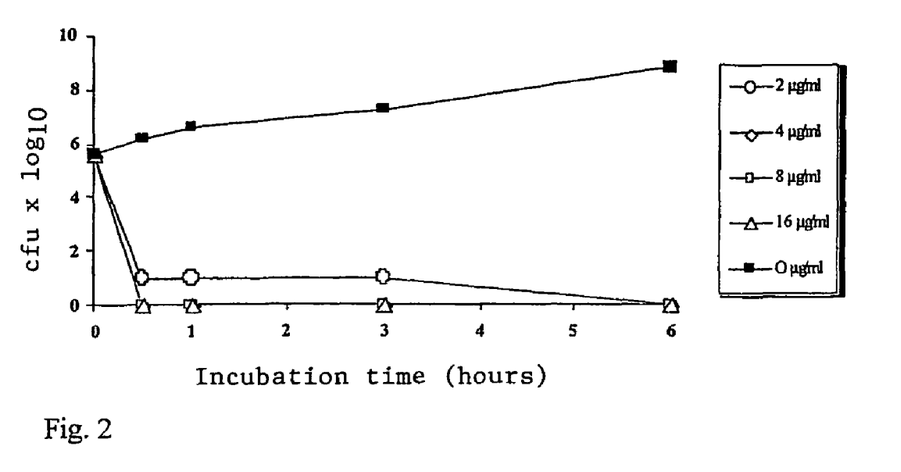
FIG. 2 is a graph showing the kinetic of bactericidal activity of peptide no. 2 of SEQ ID No. 8 on *E. coli*.
Figure 3:
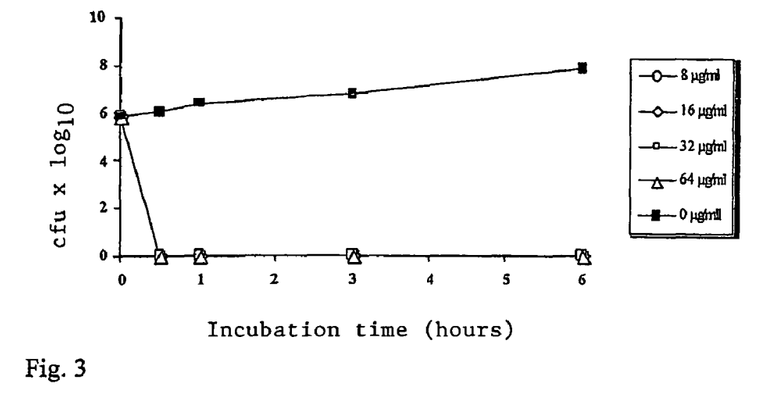
FIG. 3 is a graph showing the kinetic of bactericidal activity of peptide no. 2 of SEQ ID No. 8 on *P. aeruginosa*.

FIG. 1 presents the study of the bactericidal activity of peptide no. 1 on *E. coli*, FIG. 2 presents the study of the bactericidal activity of peptide no. 2 on *E. coli* and FIG. 3 presents the study of the bactericidal activity of peptide no. 2 on *P. aeruginosa*.

The results show that peptide no. 1 is bactericidal. There can be seen a decrease in the number of surviving bacteria greater than 3 log after 6 hours of incubation with the concentration of 64 µg/ml corresponding to 4 times the MIC reported in Table 1.

The results shown in FIGS. 2 and 3 show that peptide no. 2 has a strong bactericidal activity against *E. coli* (FIG. 2) and *P. aeruginosa* (FIG. 3).

Starting at 30 minutes of incubation of the *E. coli* bacteria, there was seen a noteworthy decrease in the number of surviving bacteria in the suspension. A decrease of 5 log was seen at the concentration of 2 µg/ml corresponding to the MIC described in table 1. For the higher concentrations, no surviving bacteria could be detected after 30 minutes of incubation.

The bactericidal activity of peptide no. 2 against *P. aeruginosa* is shown in FIG. 3 by the total absence of surviving bacteria after 30 minutes of incubation with the concentration 8 µg/ml which corresponds to the MIC described in Table 1.

C. Study of the Influence of Human Serum Proteins on the Antibacterial Activity of the Peptides An isolated colony of the bacteria *E. coli* ATCC 25922 or *P. aeruginosa* ATCC 27853 was suspended in 3 to 5 ml of Mueller-Hinton (MH) culture medium and incubated at 37° C. overnight under agitation. A culture in exponential phase of growth of the strain was prepared based on this overnight culture; the MH medium was seeded at 1/50$^{th}$ with the overnight culture and incubated for 2 hours at 37° C. under agitation. The bacterial concentration was adjusted to $\sim 5\text{-}10\cdot 10^5$ cfu/ml (colony forming units) in MH medium containing 0, 10, 25 or 50% of human serum. Fifty µl of bacterial inoculum was distributed per well (96-well polystyrene plate) containing an equal volume of peptide solution diluted by half in the MH medium supplemented by 10, 25 or 50% of human serum (peptide concentrations from 0.5 to 512 µg/ml). The MIC was determined as the lowest concentration that caused the absence of bacterial growth (absence of turbidity) after 18 hours of culture in an oven at 37° C. The MIC values were expressed in µg/ml (mg/l).

Table 3 below presents the MIC values of peptides no. 1 and no. 2 evaluated in the absence of and in the presence of human serum.

TABLE 3

| | Human serum, % | *Escherichia coli* ATCC 25922 | *Pseudomonas aeruginosa* ATCC 27853 |
|---|---|---|---|
| Peptide no. 1 | 0 | 8-32 | 64-256 |
| | 10 | 8-32 | 128 |
| | 25 | 2 | 64-128 |
| | 50 | 4 | 32-128 |
| Peptide no. 2 | 0 | 1 | 1-2 |
| | 10 | 1 | 2 |
| | 25 | 1 | 16 |
| | 50 | 1-2 | 16 |

The antibacerial activity against *P. aeruginosa* of peptide no. 1 was not modified in the presence of serum. The activity of peptide no. 1 against *E. coli* increased in the presence of 25% and 50% of human in the culture medium.

The increasing concentrations of human serum did not have any effect on the antibacterial activity of peptide no. 2 against *E. coli*. The activity of peptide no. 2 against *P. aeruginosa* was diminished in the presence of 25% and 50% of human serum.

D. Determination of the miminimal inhibitory concentration (MIC) in liquid medium for the Filamentous Fungi and Yeast Peptide concentrations tested: from 0.2 µg/ml to 100 µg/ml.

Table 4 below presents the activity of the peptides against the fungi.

TABLE 4

| Sequence MIC (µg/ml) | *C. neoformans* Cn52D | *C. albicans* ATCC 90028 | *A. fumigatus* 2001/143.02 |
|---|---|---|---|
| No. 1 | 12.5 | AND | AND |
| No. 2 | 1.56 | AND | AND |
| No. 3 | 1.56 | AND | AND |

AND: Activity Not Detected at 100 µg/ml

The results show that the 3 peptides tested are active against *Cryptococcus neoformans*.

II. Evaluation of the Hemolytic Activity of the Peptides $1\cdot 10^6$ human erythrocytes were incubated for 30 minutes with increasing concentrations of peptides (from 0 to 500

μg/ml) in a final volume of 150 μl. The hemolytic activity was evaluated by measurement of the absorbance (Abs) at the wave length 414 nm (Absorbance of hemoglobin) of the cellular supernatants. The absorbance of the supernatant after incubation of the erythrocytes in water corresponds to 100% ($Abs_{100}$) of hemolysis and the absorbance of the supernatant after incubation of the erythrocytes in PBS corresponds to 0% of hemolysis ($Abs_0$). The hemolytic activity of the peptides expressed in percentage corresponds to $(Abs_{peptide} - Abs_0)/Abs_{100} \times 100$.

Figure 4:
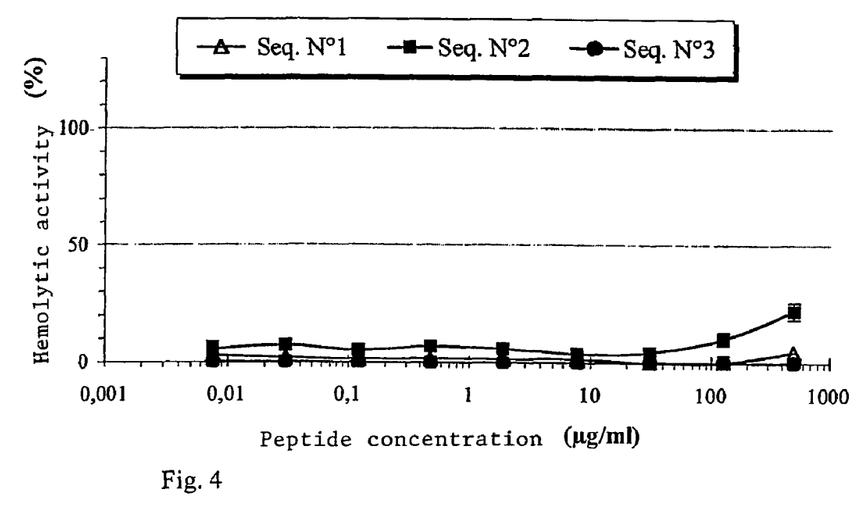
FIG. 4 is a graph showing the study of the activity of the hemolytic activities of peptides no. 1, no. 2 and no. 3 respectively of SEQ ID No. 6, SEQ ID No. 8 and SEQ ID No. 10 on human erythrocytes.

FIG. 4 presents the study of the hemolytic activity of peptides no. 1, no. 2 and no. 3 on human erythrocytes. The peptides did not exhibit hemolytic activity.

III. Evaluation of the Stability of the Peptides

A volume of 3.9 ml of human plasma was added to 100 μl of peptide no. 2 at 2 mM. The stability was determined at 37° C. After 0, 0.5, 1, 2, 4 and 6 hours, 3×200 μl were collected and added to 10 μl of internal standard (peptide no. 1) at 500 μM in water, to which 800 μl of 0.1% trifluoroacetic acid (TFA) in water was added. A volume of 1 ml of this mixture was deposited on resin C2 (EC) that had previously been equilibrated with 1 ml of 0.1% TFA in water, 1 ml of 0.1% TFA in acetonitrile and 1 ml of 0.1% TFA in water. After two washings with 1 ml of 0.1% TFA in water, the elution of peptide and of its metabolites was induced by 1 ml of 0.1% TFA in methanol. This was then dried under a stream of air and taken up in 200 μl of 0.1% TFA in water. A volume of 100 μl was analyzed by HPLC on a Luna C1 8(2) column, 3 μg, 4.6×100 mm (Phenomenex) with 0.1% TFA in water as solvent A and 0.1% TFA in acetonitrile as solvent B. A gradient of 15-45% of B in 12 minutes was used for the elution with a flow rate of 1.2 ml/min; detection was performed at 214 nm.

Figure 5:
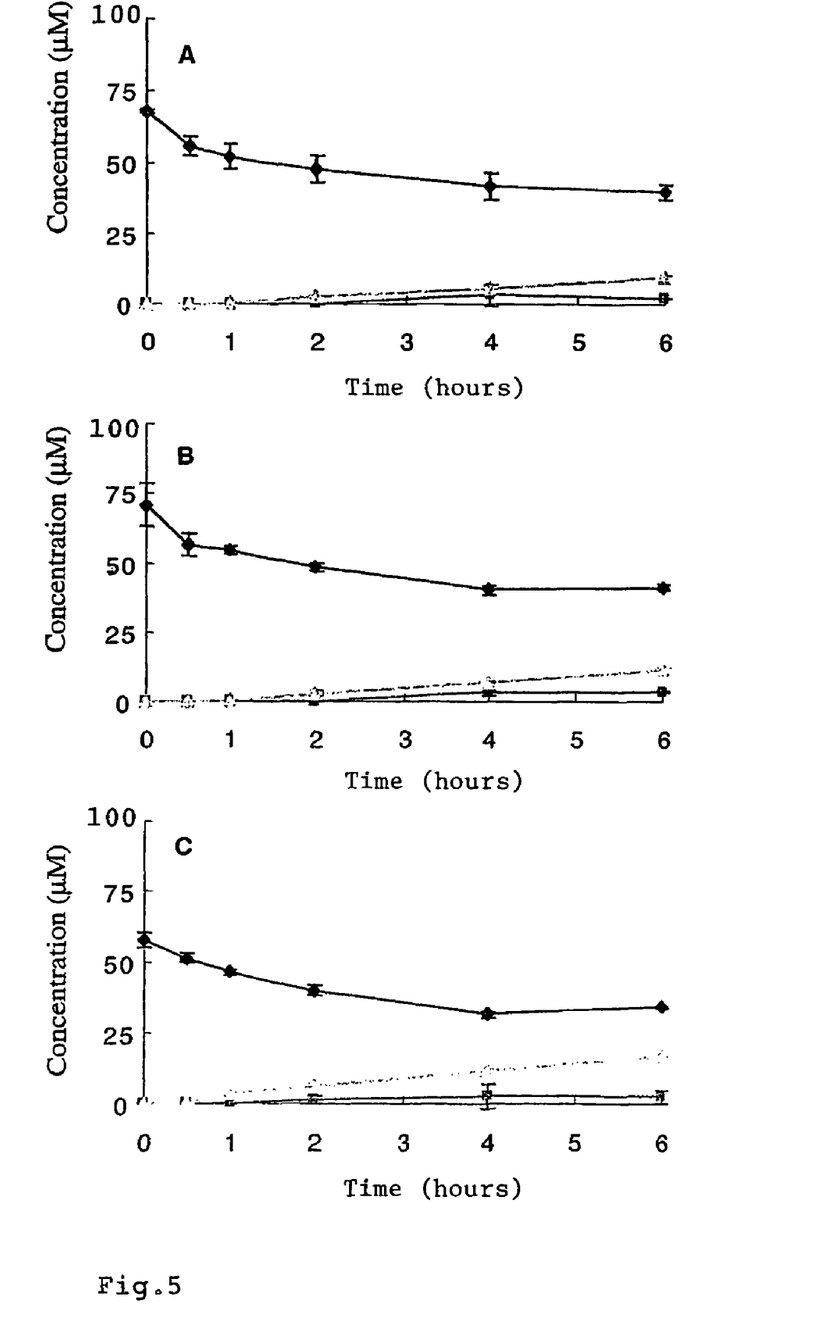
FIG. 5 is a graph showing the stability of peptide no. 2 (SEQ ID No. 8) in human plasma.

FIG. 5 presents the study of the stability of peptide 2 in three batches of human plasma obtained from different blood groups: $A^+$(A), $B^+$(B) and $O^+$(C). (solid black diamond: peptide no. 2; square and triangle: metabolites)

Two principal metabolites were generated by cleavage of peptide no. 2. Peptide no. 2 was degraded to the maximum at 41% after 6 hours of incubation in human plasma. There was no significant difference in the degradation of the peptide in relation to the blood group from which the plasma was obtained.

IV. Valuation of the in vivo Toxicity of the Peptides

The maximal tolerated dose (MTD) for each peptide was determined on female OFI mice at 28 days after an injection. The MTD was defined as the maximal nonlethal dose that could be injected. The peptides were administered by the intravenous route as a perfusion of approximately 15 minutes duration. The injection volume was 10 μl/g, the perfusion rate was 1.2 ml/hour and the excipient was a solution of NaCl at 0.8%.

Table 5 below presents the MTD values for peptides no. 1 and no. 2.

TABLE 5

| Peptide | MTD |
|---|---|
| Peptide 1 | >23.2 mg/kg |
| Peptide 2 | 13.5 mg/kg |

The invention claimed is:

1. A method for treating a fungal infection in humans, animals or plants comprising administering to the humans, animals or plants a therapeutically effective amount of an active agent comprising an isolated peptide, wherein the isolated peptide comprises:
   a first peptide sequence of formula (KLAKLAK (SEQ ID NO: 11)) in which K is lysine, L is leucine and A is alanine, and
   a second peptide sequence, wherein the second peptide sequence is KHLKKHLKKHLK (SEQ ID NO: 2)
   and in which the first peptide sequence is repeated n times and the second peptide sequence is repeated m times, n and m being whole numbers between 1 and 5.

2. A method for treating a fungal infection in humans, animals or plants comprising administering to the humans, animals or plants a therapeutically effective amount of an active agent comprising an isolated peptide, wherein the isolated peptide comprises:
   a first peptide sequence of formula (KLAKLAK (SEQ ID NO: 11)) in which K is lysine, L is leucine and A is alanine, and
   a second peptide sequence, wherein the second peptide sequence is GKRKKKGKLGKKRDP (SEQ ID NO: 3)
   and in which the first peptide sequence is repeated n times and the second peptide sequence is repeated m times, n and m being whole numbers between 1 and 5.

3. A method for treating a fungal infection in humans, animals or plants comprising administering to the humans, animals or plants a therapeutically effective amount of an active agent comprising an isolated peptide, wherein the isolated peptide comprises:

a first peptide sequence of formula (KLAKLAK (SEQ ID NO: 11)) in which K is lysine, L is leucine and A is alanine, and a second peptide sequence, wherein the second peptide sequence is VKRGLKL (SEQ ID NO: 1)

and in which the first peptide sequence is repeated n times and the second peptide sequence is repeated m times, n and m being whole numbers between 1 and 5.

4. The method according to claim 1, wherein the fungal infection is a *Cryptococcus* infection.

5. The method according to claim 4, wherein the fungal infection is a *C. neoformans* infection.

6. The method according to claim 4, wherein isolated peptide is (KLAKLAKKLAKLAKKHLKKHLKKHLK (SEQ ID NO: 8)).

7. The method according to claim 2, wherein the fungal infection is a *Cryptococcus* infection.

8. The method according to claim 7, wherein the fungal infection is a *C. neoformans* infection.

9. The method according to claim 7, wherein isolated peptide is (KLAKLAKKLAKLAKGKRKKKGKLGKKRDP (SEQ ID NO: 10)).

10. The method according to claim 3, wherein the fungal infection is a *Cryptococcus* infection.

11. The method according to claim 10, wherein the fungal infection is a *C. neoformans* infection.

12. The method according to claim 10, wherein isolated peptide is (VKRGLKLKLAKLAKKLAKLAK (SEQ ID NO 6)).

* * * * *